(12) United States Patent
Kim et al.

(10) Patent No.: US 11,471,133 B2
(45) Date of Patent: Oct. 18, 2022

(54) APPARATUS AND METHOD FOR MEASURING BLOOD CONCENTRATION OF ANALYTE

(71) Applicant: SAMSUNG ELECTRONICS CO., LTD., Suwon-si (KR)

(72) Inventors: Sang Kyu Kim, Yongin-si (KR); Jun Ho Lee, Incheon (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 443 days.

(21) Appl. No.: 16/567,706

(22) Filed: Sep. 11, 2019

(65) Prior Publication Data
US 2020/0077989 A1 Mar. 12, 2020

(30) Foreign Application Priority Data
Sep. 11, 2018 (KR) .................. 10-2018-0108501

(51) Int. Cl.
| | | |
|---|---|---|
| *A61B 5/1455* | (2006.01) | |
| *A61B 10/00* | (2006.01) | |
| *A61B 5/145* | (2006.01) | |
| *G01N 21/84* | (2006.01) | |

(52) U.S. Cl.
CPC ........ *A61B 10/0064* (2013.01); *A61B 5/1455* (2013.01); *A61B 5/14521* (2013.01); *G01N 21/8483* (2013.01)

(58) Field of Classification Search
CPC .............. A61B 5/1455; A61B 5/14521; A61B 10/0064
See application file for complete search history.

(56) References Cited

U.S. PATENT DOCUMENTS

| | | |
|---|---|---|
| 7,066,884 B2 | 6/2006 | Custer et al. |
| 7,725,149 B2 | 5/2010 | Peyser et al. |
| 2006/0004271 A1 | 1/2006 | Peyser et al. |
| 2007/0027383 A1 | 2/2007 | Peyser et al. |
| 2010/0063372 A1 | 3/2010 | Potts et al. |

(Continued)

FOREIGN PATENT DOCUMENTS

| | | |
|---|---|---|
| KR | 10-2007-0043768 A | 4/2007 |
| KR | 10-2016-0075230 A | 6/2016 |

(Continued)

OTHER PUBLICATIONS

Nurul Akmal Binti Abd Salam et al., "The Evolution of Non-invasive Blood Glucose Monitoring System for Personal Application", Journal of Telecommunication, Electronic and Computer Engineering, vol. 8, No. 1, 2016, pp. 59-65.

(Continued)

*Primary Examiner* — Marjan Fardanesh
(74) *Attorney, Agent, or Firm* — Sughrue Mion, PLLC

(57) ABSTRACT

An apparatus for estimating blood concentration of an analyte may include a sweat collector configured to collect sweat from a skin surface of a user. The apparatus may include an optical sensor configured to emit light rays of different wavelengths towards the collected sweat, and detect an optical signal reflected by the collected sweat. The apparatus may include a processor configured to estimate the blood concentration of the analyte based on the detected optical signal.

15 Claims, 11 Drawing Sheets

(56) References Cited

U.S. PATENT DOCUMENTS

2015/0330893 A1* 11/2015 Larson ............... A61B 5/14552
600/301
2016/0174853 A1 6/2016 Cho et al.

FOREIGN PATENT DOCUMENTS

| KR | 10-2016-0107086 A | 9/2016 |
| KR | 10-2018-0002550 A | 1/2018 |

OTHER PUBLICATIONS

Danielle Bruen et al., "Glucose Sensing for Diabetes Monitoring: Recent Developments", Sensors, 17, 1866, MDPI, Aug. 12, 2017, pp. 1-21.

Hyunjae Lee et al., "Wearable/disposable sweat-based glucose monitoring device with multistage transdermal drug delivery module", Science Advances, vol. 3, Mar. 8, 2017, 9 pages.

Ahyeon Koh et al., "A soft, wearable microfluidic device for the capture, storage, and colorimetric sensing of sweat", Science Translational Medicine, vol. 8, Nov. 23, 2016, 15 pages.

Mallika Bariya et al., "Wearable sweat sensors", Nature Electronics, vol. 1, Macmillan Publishers Limited, Mar. 2018, pp. 160-171.

* cited by examiner

APPARATUS AND METHOD FOR MEASURING BLOOD CONCENTRATION OF ANALYTE

CROSS-REFERENCE TO RELATED APPLICATION(S)

This application is based on and claims priority under 35 U.S.C. § 119 to Korean Patent Application No. 10-2018-0108501, filed on Sep. 11, 2018, in the Korean Intellectual Property Office, the disclosure of which is incorporated by herein in its entirety.

BACKGROUND

1. Field

The disclosure relates to an apparatus and method for non-invasively measuring blood concentration of analyte.

2. Description of Related Art

Diabetes mellitus is a chronic disease which is difficult to treat and causes various complications, and hence a blood sugar level should be checked regularly to prevent any complications. When insulin is administered, blood sugar should be checked in order to prevent hypoglycemia and control the insulin dosage. Generally, measuring blood sugar requires an invasive method such as drawing blood with a finger prick. The method of measuring blood sugar in an invasive manner has high reliability of measurement, but the use of injection may cause pain during blood sampling, inconvenience, and a risk of infection. Recently, a method of non-invasive measurement of blood sugar using an optical sensor, without directly collecting blood, has been studied.

SUMMARY

The following description relates to an apparatus and method for non-invasively measuring blood concentration of analyte.

Additional aspects will be set forth in part in the description which follows and, in part, will be apparent from the description, or may be learned by practice of the presented embodiments According to an aspect of the disclosure, there is provided an apparatus for estimating a blood concentration of an analyte including a sweat collector configured to collect sweat from a skin surface of a user; an optical sensor configured to emit light rays of different wavelengths towards the collected sweat, and detect an optical signal reflected by the collected sweat; and a processor configured to estimate the blood concentration of the analyte based on the detected optical signal.

The sweat collector may include a sweat collecting layer configured to collect the sweat from the skin surface of the user, and a sweat storing layer configured to store the collected sweat.

The sweat collector may include a light reflecting layer configured to scatter light.

The light reflecting layer may be interposed between the sweat collecting layer and the sweat storing layer.

The light reflecting layer may be disposed below the sweat collecting layer.

The analyte may include at least one of glucose, triglyceride, cholesterol, protein, lactate, ethanol, uric acid, and ascorbic acid.

The processor may reconstruct a sweat spectrum based on the detected optical signal, and estimate the blood concentration of the analyte by analyzing the reconstructed sweat spectrum.

The processor may estimate concentration of the analyte in the collected sweat based on the reconstructed sweat spectrum and using a sweat analyte concentration estimation model, and estimate the blood concentration of the analyte based on the estimated concentration of the analyte in the sweat using a sweat analyte concentration-blood concentration relationship model.

The processor may estimate the blood concentration of the analyte based on the reconstructed sweat spectrum and using a blood concentration estimation model.

The apparatus may include an output interface configured to output the estimated blood concentration.

According to an aspect of the disclosure, there is provided a method of estimating a blood concentration of an analyte by collecting sweat from a skin surface of a user; emitting light rays of different wavelengths towards the collected sweat, and detecting an optical signal reflected by the collected sweat; and estimating the blood concentration of the analyte based on the detected optical signal.

The analyte may include at least one of glucose, triglyceride, cholesterol, protein, lactate, ethanol, uric acid, and ascorbic acid.

The estimating of the blood concentration of the analyte comprises reconstructing a sweat spectrum based on the detected optical signal, and estimating the blood concentration of the analyte by analyzing the reconstructed sweat spectrum.

The estimating of the blood concentration of the analyte comprises estimating concentration of the analyte in the collected sweat based on the sweat spectrum and using a sweat analyte concentration estimation model, and estimating the blood concentration based on the estimated concentration of the analyte in the collected sweat using a sweat analyte concentration-blood concentration relationship model.

The estimating of the blood concentration of the analyte comprises estimating the blood concentration of the analyte from the sweat spectrum using a blood concentration estimation model.

The method may include outputting the estimated blood concentration.

Other features and aspects will be apparent from the following detailed description, the drawings, and the claims.

BRIEF DESCRIPTION OF THE DRAWINGS

The above and other aspects, features, and advantages of certain embodiments of the present disclosure will be more apparent from the following description taken in conjunction with the accompanying drawings, in which.

Figure 1:
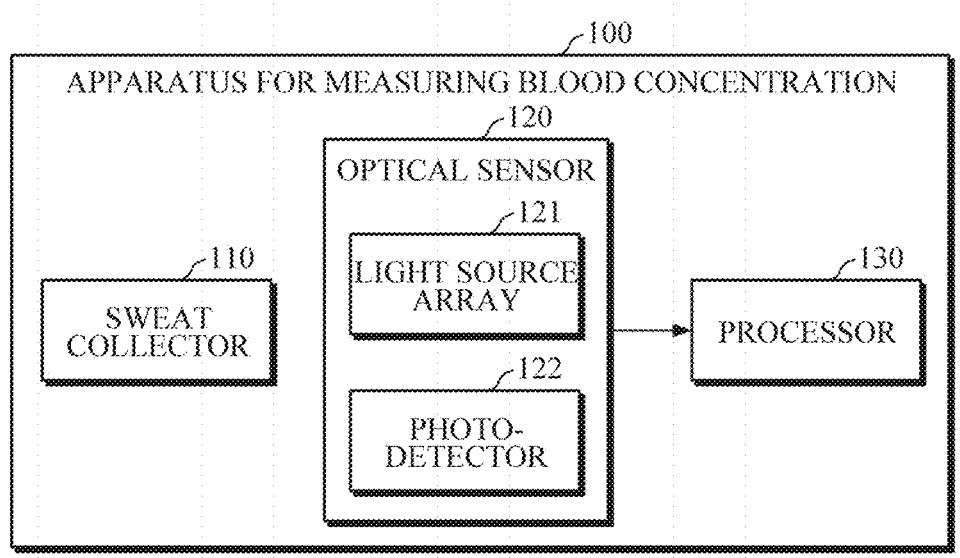
FIG. 1 is a block diagram illustrating an apparatus for measuring blood concentration according to an embodiment.

Throughout the drawings and the detailed description, unless otherwise described, the same drawing reference numerals will be understood to refer to the same elements, features, and structures. The relative size and depiction of these elements may be exaggerated for clarity, illustration, and convenience.

DETAILED DESCRIPTION

The following detailed description is provided to assist the reader in gaining a comprehensive understanding of the methods, apparatuses, and/or systems described herein. Various changes, modifications, and equivalents of the systems, apparatuses, and/or methods described herein should be apparent to those of ordinary skill in the art. In the following description, a detailed description of known functions and configurations incorporated herein may be omitted when such description may obscure the subject matter with unnecessary detail.

It should be noted that in some alternative implementations, the functions/acts noted in the blocks may occur in a different order than as shown in the flowcharts. For example, two blocks shown in succession may in fact be executed substantially concurrently, or the blocks may be executed in the reverse order, depending upon the functionality/acts involved.

Terms described herein are selected by considering functions in the embodiment, and meanings of the terms may vary depending on, for example, a user or operator's intentions or customs. Therefore, in the following embodiments, when terms are specifically defined, the meanings of the terms should be interpreted based on the provided definitions, and otherwise, should be interpreted based on general meanings recognized by those skilled in the art.

It should be understood that, although the terms "first," "second," etc. may be used herein to describe various elements, these elements should not be limited by these terms. These terms may be used to distinguish one element from another. Also, the singular forms of terms are intended to include the plural forms of the terms as well, unless the context clearly indicates otherwise. In the specification, unless explicitly described to the contrary, the word "comprise" and variations such as "comprises" or "comprising" should be understood to imply the inclusion of stated elements but not the exclusion of any other elements. Terms such as "unit" and "module" may denote units that process at least one function or operation, and may refer to units or modules that may be implemented by hardware, software, or a combination of hardware and software.

Figure 2:
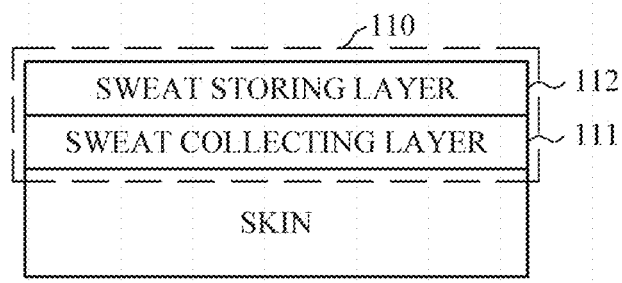
FIG. 2 is a diagram illustrating a sweat collector according to an embodiment.
Figure 3:
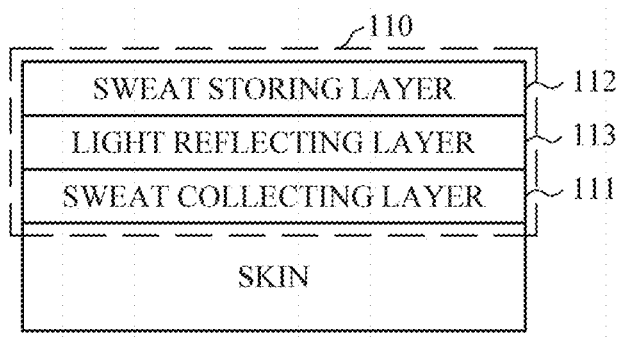
FIG. 3 is a diagram illustrating a sweat collector according to an embodiment.
Figure 4:
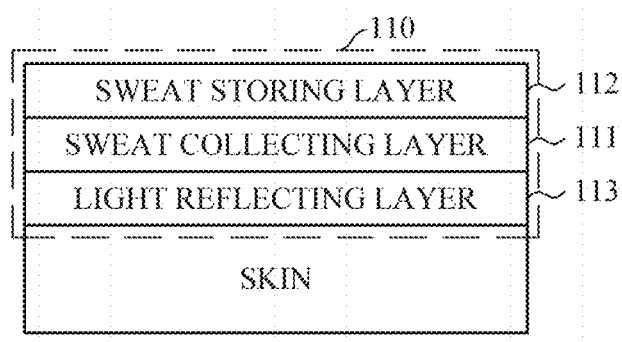
FIG. 4 is a diagram illustrating a sweat collector according to an embodiment.
Figure 5:
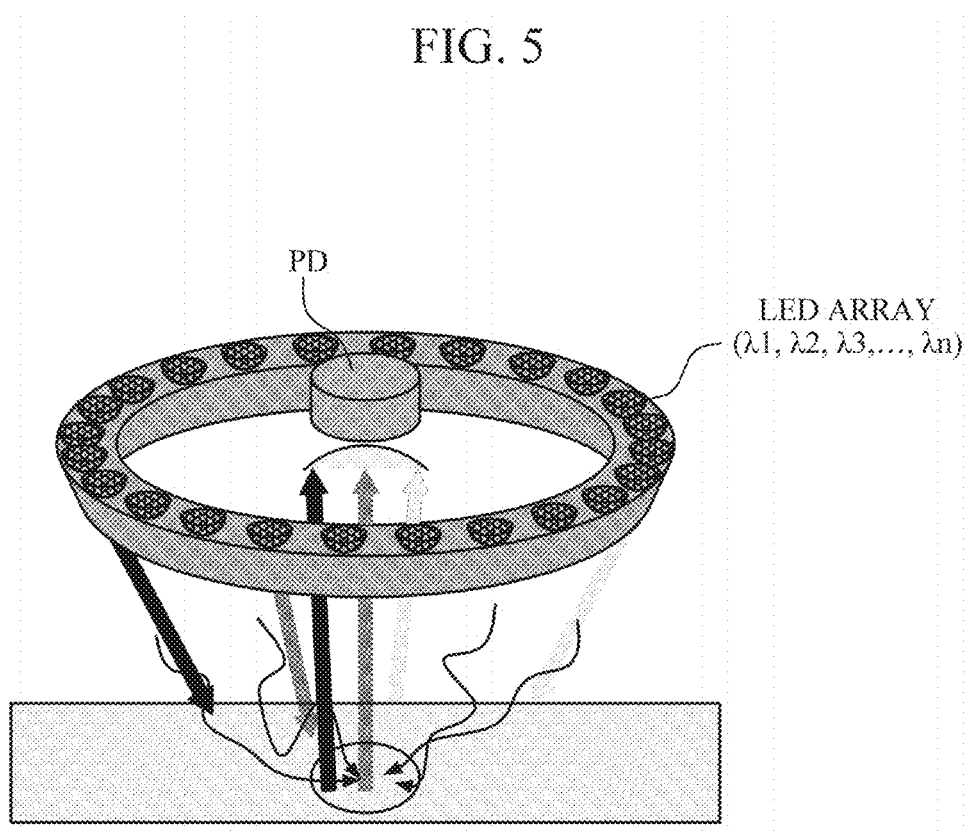
FIG. 5 is a diagram illustrating an arrangement of a light source array and a photodetector according to an embodiment.

FIG. 1 is a block diagram illustrating an apparatus for measuring blood concentration according to an embodiment, FIGS. 2 through 4 are diagrams illustrating a sweat collector according to various embodiments, and FIG. 5 is a diagram illustrating an arrangement of a light source array and a photodetector according to an embodiment.

The apparatus 100 for measuring blood concentration as shown in FIG. 1 may be an apparatus capable of collecting sweat from the skin and non-invasively estimating blood concentration of analyte using the collected sweat. Further, the apparatus 100 may be mounted in an electronic device. The electronic device may include a mobile phone, a smartphone, a tablet computer, a notebook computer, a personal digital assistant (PDA), a portable multimedia player (PMP), a navigation system, an MP3 player, a digital camera, a wearable device, and the like. The wearable device may include wearable devices of a wrist watch type, a wrist band type, a ring type, a belt type, a necklace type, an ankle band type, a thigh band type, a forearm band type, and the like. However, the electronic device and the wearable devices are not limited to the aforementioned examples.

Referring to FIG. 1, the apparatus 100 for measuring blood concentration may include a sweat collector 110, an optical sensor 120, and a processor 130.

The sweat collector 110 may collect sweat from the skin of a user. For example, the sweat collector 110 may non-invasively collect sweat from a skin surface of a user.

According to an embodiment, and as shown in FIG. 2, the sweat collector 110 may include a sweat collecting layer 111, and a sweat storing layer 112.

The sweat collecting layer 111 may collect sweat discharged from sweat glands of the skin. The sweat collecting layer 111 may be formed of a macromolecular polymer (e.g., polydimethylsiloxane (PDMS)) and hence may include microfluidic channels. Additionally, or alternatively, the sweat collecting layer 111 may be implemented as a porous structure.

The sweat storing layer 112 may store the sweat collected by the sweat collecting layer 111. The sweat storing layer 112 may be formed of a transparent material to reduce an effect on light emitted from the optical sensor 120.

According to an embodiment, and as shown in FIGS. 3 and 4, the sweat collector 110 may further include a light reflecting layer 113 to improve the scattering of light. The light reflecting layer 113 may be interposed between the sweat collecting layer 111 and the sweat storing layer 112 (e.g., as shown in FIG. 3), or may be disposed below the sweat collecting layer 111 (e.g., as shown in FIG. 4). When the light reflecting layer 113 is disposed below the sweat collecting layer 111, the sweat collecting layer 111 may be formed of a transparent material to reduce an effect on light emitted from the optical sensor 120.

The sweat collector 110 may include an outlet via which the collected sweat is discharged when the measurement is completed.

The optical sensor 120 may emit light towards the collected sweat, and detect an optical signal reflected by the collected sweat. As shown in FIG. 1, the optical sensor 120 may include a light source array 121 including multiple light sources, and a photodetector 122.

Each of the light sources in the light source array 121 may emit a light ray of a different wavelength to the collected sweat. For example, each of the light sources may emit a light ray of a predetermined wavelength such as, for example, a near infrared ray (NIR), to the collected sweat. However, the wavelength of light emitted from each of the light sources may vary according to the measurement purpose or a type of analyte. In addition, each of the light sources might not necessarily be composed of a single light emitter, and may be composed of multiple light emitters. Each of the light sources may include a light emitting diode (LED), a laser diode, a phosphor, or the like.

The photodetector 122 may detect an optical signal reflected or scattered by the collected sweat. The photodetector 122 may convert the detected optical signal into an electrical signal, and transmit the electrical signal to the processor 130. According to an embodiment, the photodetector 122 may include a photodiode, a photo transistor, a charge-coupled device (CCD), or the like. The photodetector 122 might not necessarily be composed of a single element, and may be configured in the form of an array including multiple elements.

The light sources of the light source array 121 may be arranged to surround a periphery of the photodetector 122. For example, the light source array 121 may be arranged concentrically around the photodetector 122 to surround the periphery of the photodetector 122.

For example, and referring to FIG. 5, a photodiode PD may be disposed at a center of the optical sensor 120, and n LED arrays may be concentrically disposed around the photodiode PD. Each of the LEDs may be preset to include a different peak wavelength, such as $\lambda_1, \lambda_2, \lambda_3, \ldots$, or $\lambda_n$. Each of the LEDs may be sequentially driven in response to a predetermined control signal and emit light of the set peak wavelength to the collected sweat, and the photodiode PD may detect light reflected by the collected sweat.

The processor 130 may control an overall operation of the apparatus 100 for measuring blood concentration.

The processor 130 may control the light source array 121 to emit light towards the sweat collected by the sweat collector 110. The processor 130 may control an ON/OFF state of each light source of the light source array 121 in a time-division manner. Additionally, or alternatively, the processor 130 may control the light sources to simultaneously emit light by simultaneously turning on the power of the light sources, or may classify the light sources into groups according to a preset peak wavelength, and control each group of light sources in a time-division manner. However, the method of controlling the light sources may be adjusted based on a variety of factors, such as a status of a battery, the application field of the optical sensor 120, a size of the photodetector 122, or the like.

In this case, conditions for driving light sources, which include the time of light emission of each light source, the driving order of the light sources, a current intensity, and the pulse duration, may be set in advance, and the processor 130 may control the driving of the light sources based on the preset conditions for driving light sources.

The processor 130 may reconstruct a sweat spectrum based on the optical signal detected by the optical sensor 120, and estimate blood concentration of analyte by analyzing the reconstructed sweat spectrum. In this case, the analyte may include glucose, triglyceride, cholesterol, protein, lactate, ethanol, uric acid, ascorbic acid, and the like. In a situation where the analyte is glucose, the blood concentration of the analyte may be blood sugar.

According to an embodiment, the processor 130 may estimate the concentration of analyte in the sweat from the sweat spectrum using a sweat analyte concentration estimation model defining a relationship between a sweat spectrum and concentration of analyte in the sweat, and estimate the blood concentration of analyte using a sweat analyte concentration-blood concentration relationship model defining a relationship between the concentration of analyte in sweat and blood concentration. In this case, the sweat analyte concentration estimation model may be generated by training the model using the sweat spectrum and the concentration of analyte in the sweat corresponding to the sweat spectrum as training data. In addition, the sweat analyte concentration-blood concentration relationship model may be generated by training the model using the sweat analyte concentration and the blood concentration corresponding to the sweat analyte concentration as training data.

According to an embodiment, the processor 130 may estimate blood concentration of the analyte from the sweat spectrum using a blood concentration estimation model that defines a relationship between a sweat spectrum and blood concentration of analyte. In this case, the blood concentration estimation model may be generated by training the model using the sweat spectrum and the blood concentration of analyte corresponding to the sweat spectrum as training data.

In this case, a training algorithm may include a machine learning algorithm, a net analyte signal (NAS) algorithm, and the like, and the sweat analyte concentration estimation model, the sweat analyte concentration-blood concentration relationship model, and/or the blood concentration estimation model may be generated in advance and stored in an internal or external database.

According to an embodiment, the sweat collector 110 may include a reagent that reacts with ions (e.g., a sodium cation ($Na^+$), a potassium cation ($K^+$), a chloride anion ($Cl^-$), a calculation cation ($Ca^{2+}$), and a hydrogen cation ($H^+$)). Ions present in the sweat may react with the reagent to change the color of the sweat, and the optical sensor 120 may emit light towards the color-changed sweat and detect an optical signal reflected by the color-changed sweat. The processor 130 may estimate the concentration of ions in the sweat or the blood concentration by reconstructing and analyzing a spectrum of the color-changed sweat based on the detected optical signal.

Figure 6:
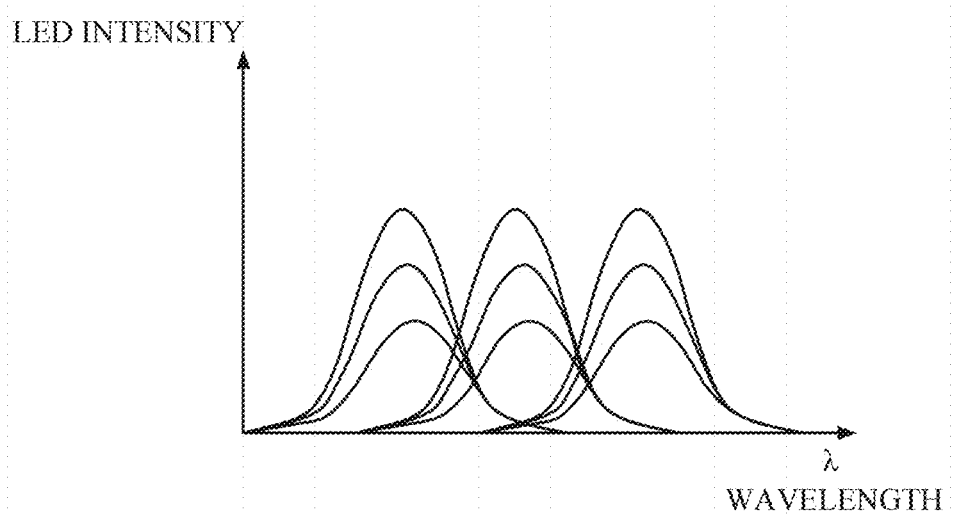
FIGS. 6 through 8 are diagrams for describing a process of reconstructing a spectrum in a processor according to an embodiment.
Figure 7:
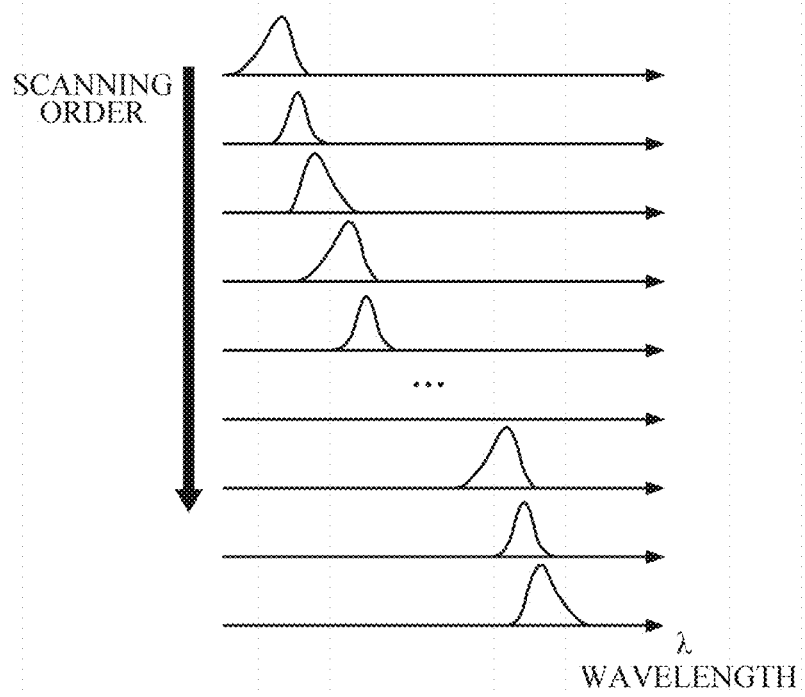
Figure 8:
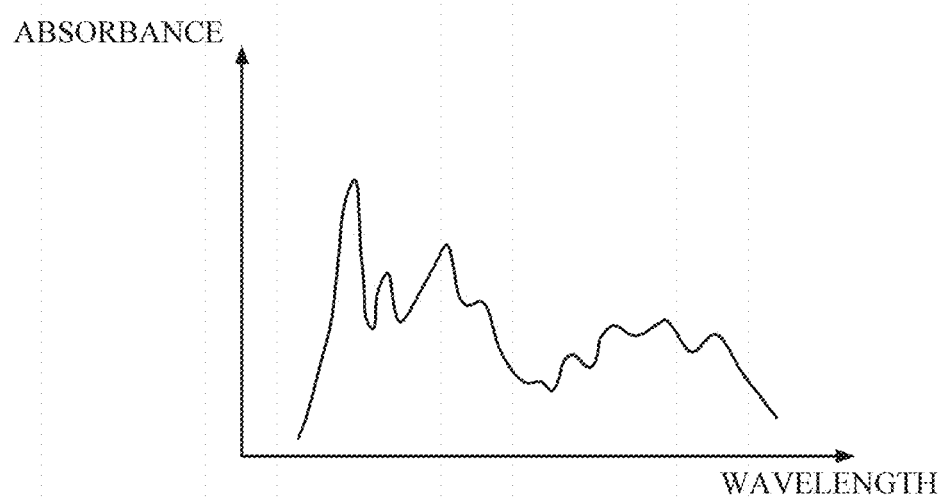

FIGS. 6 through 8 are diagrams for describing a process of reconstructing a spectrum in the processor 130.

Referring to FIGS. 5 and 6, the light source array 121 may be formed as an LED array composed of n LEDs, and a peak wavelength of each LED may be set to $\lambda_1, \lambda_2, \lambda_3, \ldots$, or $\lambda_n$ based on conditions for driving a light source (e.g., temperature, current intensity, pulse duration, and the like).

Referring to FIG. 7, the processor 130 sequentially drives each light source to emit light based on a preset driving order, the conditions for driving a light source, and the like, and the photodetector PD detects light reflected by the collected sweat. In this case, to the processor 130 may drive some of the light sources, or may classify the light sources into groups and drive each group in a time-division manner.

Referring to FIG. 8, the processor 130 receives the optical signal detected from the photodetector PD, and reconstructs the sweat spectrum. In this case, the processor 130 may reconstruct the spectrum using Equation 1 shown below.

$$y_\alpha = (\alpha E + A^T A)^{-1} A^T p \qquad \text{(Equation 1)}$$

Referring to Equation 1, $\alpha$ denotes a spectrum reconstruction parameter, E denotes a unit matrix, A denotes a light source spectrum measured according to a driving condition for each light source, p denotes an intensity of the optical signal measured by the photodetector, and $y_\alpha$ denotes a reconstructed spectrum. In this case, the light source spectrum is a spectrum of light emitted from each light source, and information associated with the light source spectrum may be stored in advance in an internal or external database.

Figure 9:
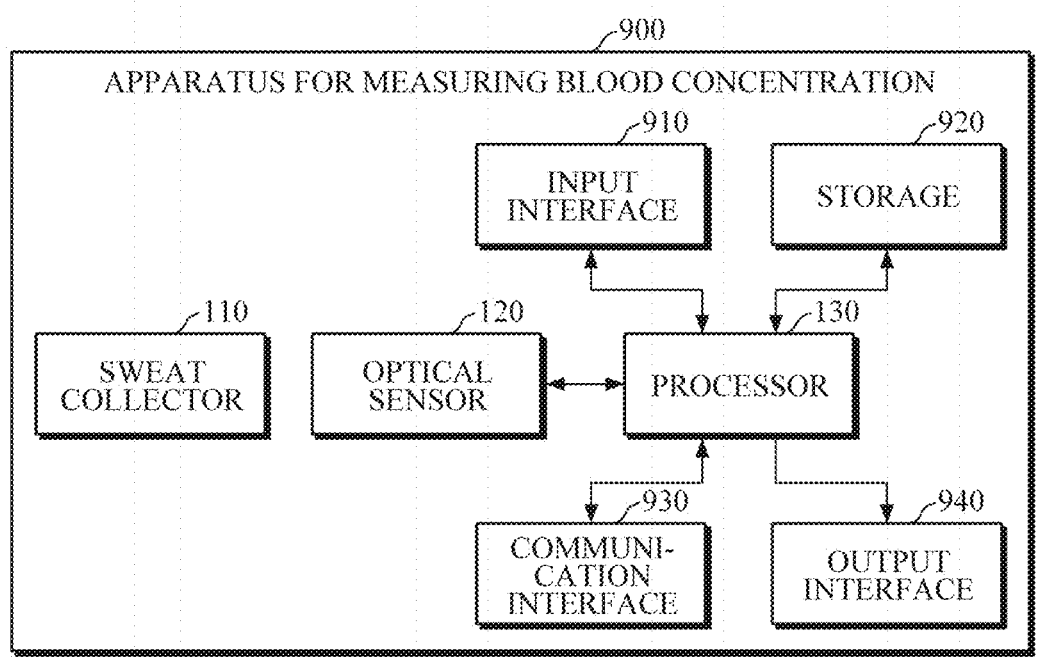
FIG. 9 is a block diagram illustrating an apparatus for measuring blood concentration according to an embodiment.

FIG. 9 is a block diagram illustrating an apparatus for measuring blood concentration according to an embodiment. The apparatus 900 for measuring blood concentration is an apparatus configured to collect sweat from the skin and non-invasively estimate blood concentration of analyte using the collected sweat. Further, the apparatus 900 may be mounted in an electronic device. The electronic device may include a mobile phone, a smartphone, a tablet computer, a notebook computer, a PDA, a PMP, a navigation system, an MP3 player, a digital camera, a wearable device, and the like. The wearable device may include wearable devices of a wrist watch type, a wrist band type, a ring type, a belt type, a necklace type, an ankle band type, a thigh band type, a forearm band type, and the like. However, the electronic device and the wearable devices are not limited to the aforementioned examples.

Referring to FIG. 9, the apparatus 900 may include a sweat collector 110, an optical sensor 120, a processor 130, an input interface 910, a storage 920, a communication interface 930, and an output interface 940. Here, the sweat collector 110, the optical sensor 120, and the processor 130 may be substantially the same as described with reference to FIGS. 1 through 8, and thus detailed descriptions thereof are not reiterated.

The input interface 910 may receive various operation signals based on a user input. According to an embodiment, the input interface 910 may include a key pad, a dome switch, a touch pad (e.g., a resistive/capacitive touch pad), a jog wheel, a jog switch, a hardware button, and the like. In particular, when a touch pad has a layered structure with a display, this structure may be referred to as a touch screen.

Programs or commands for operation of the apparatus 900 for measuring blood concentration may be stored in the storage 920, and data input to and output from the apparatus 900 for measuring blood concentration may be stored in the storage 920. In addition, a reconstructed sweat spectrum, various models (e.g., a sweat analyte concentration estimation model, a sweat analyte concentration-blood concentration relationship model, and/or a blood concentration estimation model), a result of estimating blood concentration of analyte, and the like, may be stored in the storage 920. The storage 920 may include at least one type of storage medium, such as a flash memory type, a hard disk type, a multimedia card micro type, a card type memory (e.g., SD or XD memory) random access memory (RAM), static random access memory (SRAM), read-only memory (ROM), electrically erasable programmable read-only memory (EEPROM), programmable read-only memory (PROM), a magnetic memory, a magnetic disk, and an optical disk. In addition, the apparatus 900 for measuring blood concentration may communicate with an external storage medium, such as a web storage that performs the storage function of the storage 920 on the Internet.

The communication interface 930 may communicate with an external device. For example, the communication interface 930 may transmit the data that is input to the apparatus 900, stored data, processed data, and the like, to the external device, and may receive various data to estimate blood concentration of analyte from the external device.

In this case, the external device may be medical equipment which uses the data input to, stored in, or processed by the apparatus 900 for measuring blood concentration, or a printer or a display device to output a result. In addition, the external device may include a digital TV, a desktop computer, a mobile phone, a smartphone, a tablet computer, a notebook computer, a PDA, a PMP, a navigation system, an MP3 player, a digital camera, a wearable device, and the like, but is not limited thereto.

The communication interface 930 may communicate with the external device using Bluetooth communication, Bluetooth low energy (BLE) communication, near field communication (NFC), wireless local access network (WLAN) communication, ZigBee communication, infrared data association (IrDA) communication, wireless fidelity (Wi-Fi) communication, ultra-wideband (UWB) communication, Ant+ communication, Wi-Fi direct (WFD) communication, radio frequency identification (RFID) communication, third generation (3G) communication, fourth generation (4G) communication, and fifth generation (5G) communication. However these are merely examples, and the types of communication are not limited thereto.

The output interface 940 may output the data input to, stored in, and processed by the apparatus 900 for measuring blood concentration. According to an embodiment, the output interface 940 may output the data by the apparatus 900 for measuring blood concentration using at least one of an audible method, a visual method, and a tactile method. To this end, the output interface 940 may include a display, a speaker, a vibrator, and the like.

Figure 10:
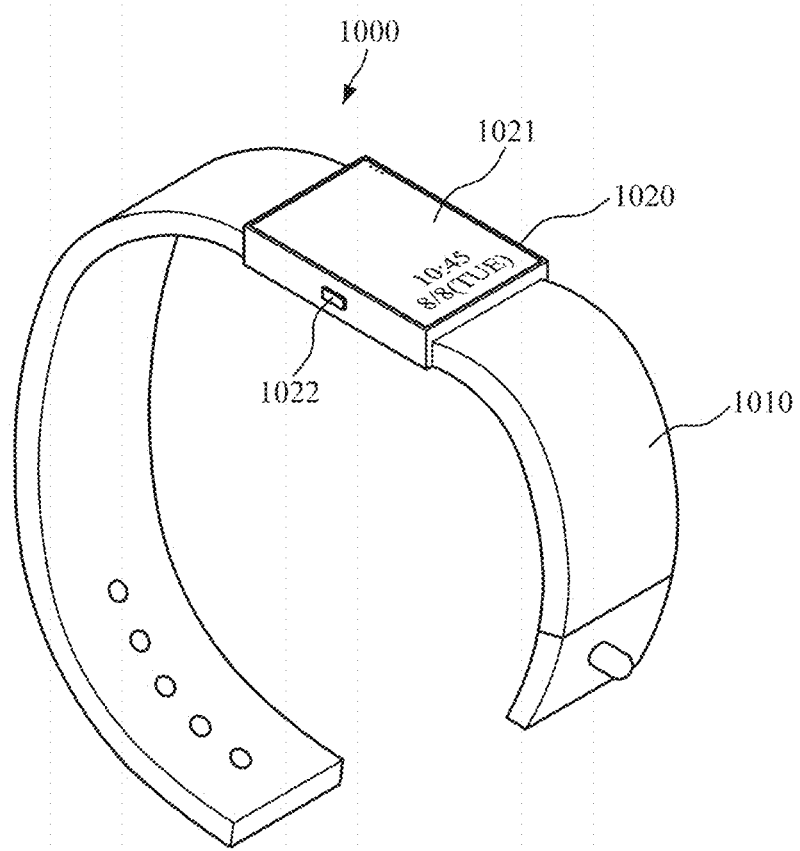
FIG. 10 is a diagram illustrating a wrist-type wearable device according to an embodiment.

FIG. 10 is a diagram illustrating a wrist-type wearable device according to an embodiment.

Referring to FIG. 10, the wrist-type wearable device 1000 may include a strap 1010, and a main body 1020.

The strap 1010 may be divided into two members that are connected to each end of the main body 1020 and that are configured to be coupled to each other, or may be integrally formed in the form of a smart band. The strap 1010 may be formed of a flexible material to be worn on the user's wrist and wrap around the user's wrist.

The main body 1020 may include the above-described apparatuses 100 or 900 for measuring blood concentration disposed therein. In addition, a battery for supplying power to the wrist-type wearable device 1000 and the apparatuses 100 or 900 for measuring blood concentration may be embedded in the main body 1020.

A sweat collector 110 and an optical sensor 120 may be mounted in a lower part of the main body 1020 such that the sweat collector 110 and the optical sensor 120 are exposed to the wrist of the user. Accordingly, when the user wears the wrist-type wearable device 1000, the sweat collector 110 is naturally brought into contact with the skin of the user. In this case, the optical sensor 120 may emit light towards sweat collected by the sweat collector 110, and detect an optical signal reflected by or scattered from the sweat.

The wrist-type wearable device 1000 may further include a display 1021 and an input interface 1022, which are disposed in the main body 1020. The display 1021 may display data processed by the wrist-type wearable device 1000, data processed by the apparatuses 100 or 900 for measuring blood concentration, and processing result data. The input interface 1022 may receive various operation signals from the user based on a user input.

Figure 11:
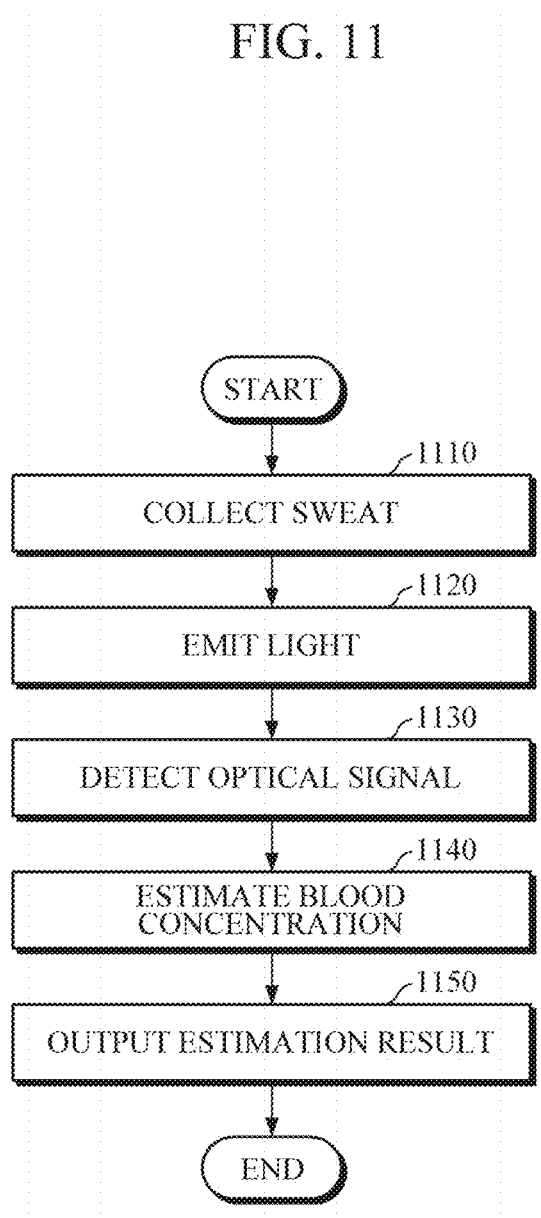
FIG. 11 is a flowchart illustrating a method of measuring blood concentration according to an embodiment.

FIG. 11 is a flowchart illustrating a method of measuring blood concentration according to an embodiment. The method shown in FIG. 11 may be performed by the apparatus 100 and/or apparatus 900 for measuring blood concentration as shown in FIGS. 1 and 9, respectively.

Referring to FIG. 11, the apparatus for measuring blood concentration may collect sweat from the skin of a user (step 1110).

The apparatus may emit light rays of different wavelengths towards the collected sweat (step 1120), and detect an optical signal reflected by the collected sweat (step 1130).

The apparatus may estimate blood concentration of analyte based on the detected optical signal. The analyte may include glucose, triglyceride, cholesterol, protein, lactate, ethanol, uric acid, ascorbic acid, and the like.

For example, the apparatus for measuring blood concentration may reconstruct a sweat spectrum using Equation 1 as described elsewhere herein based on the detected optical signal, and estimate blood concentration of the analyte by analyzing the reconstructed sweat spectrum.

According to an embodiment, the apparatus for measuring blood concentration may estimate concentration of analyte in sweat from a sweat spectrum using a sweat analyte concentration estimation model, which defines a relationship between a sweat spectrum and concentration of analyte in sweat, and may estimate blood concentration of analyte using a sweat analyte concentration-blood concentration relationship model, which defines a relationship between concentration of analyte in sweat and blood concentration. In this case, the sweat analyte concentration estimation model may be generated by training the model using the sweat spectrum and the concentration of analyte in the sweat corresponding to the sweat spectrum as training data. In addition, the sweat analyte concentration-blood concentration relationship model may be generated by training the model using the sweat analyte concentration and the blood concentration corresponding to the sweat analyte concentration as training data.

According to an embodiment, the apparatus for measuring blood concentration may estimate blood concentration of analyte from a sweat spectrum using a blood concentration estimation model, which defines a relationship between a sweat spectrum and blood concentration of analyte. In this case, the blood concentration estimation model may be generated by training the model using the sweat spectrum and blood concentration of analyte corresponding to the sweat spectrum as training data.

The apparatus for measuring blood concentration may output a result of estimating blood concentration of analyte (step 1150). For example, the apparatus may output the result of estimating blood concentration of analyte using at least one of an audible method, a visual method, and a tactile method.

The embodiments may be implemented as computer readable code stored in a non-transitory computer-readable medium. Code and code segments constituting the computer program can be inferred by a person skilled in the art. The computer-readable medium includes all types of recording media in which computer readable data is stored. Examples of the computer-readable medium include a ROM, a RAM, a CD-ROM, a magnetic tape, a floppy disk, and an optical data storage. Further, the recording medium may be implemented in the form of a carrier wave such as Internet transmission. In addition, the computer-readable medium may be distributed to computer systems over a network, in which computer-readable code may be stored and executed in a distributed manner.

A number of examples have been described above. Nonetheless, it should be understood that various modifications may be made. For example, suitable results may be achieved if the described techniques are performed in a different order and/or if components in a described system, architecture, device, or circuit are combined in a different manner and/or replaced or supplemented by other components or their equivalents. Accordingly, other implementations are within the scope of the following claims.

What is claimed is:

1. An apparatus for estimating a blood concentration of an analyte, comprising:
    a sweat collector configured to collect sweat from a skin surface of a user;
    an optical sensor configured to emit light rays of different wavelengths towards the collected sweat, and detect an optical signal reflected by the collected sweat; and
    a processor configured to estimate the blood concentration of the analyte based on the detected optical signal,
    wherein the sweat collector comprises a sweat collecting layer configured to collect the sweat from the skin surface of the user, a sweat storing layer configured to store the collected sweat, and a light reflecting layer configured to scatter light.

2. The apparatus of claim 1, wherein the light reflecting layer is interposed between the sweat collecting layer and the sweat storing layer.

3. The apparatus of claim 1, wherein the light reflecting layer is disposed below the sweat collecting layer.

4. The apparatus of claim 1, wherein the analyte includes at least one of glucose, triglyceride, cholesterol, protein, lactate, ethanol, uric acid, and ascorbic acid.

5. The apparatus of claim 1, wherein the processor is configured to reconstruct a sweat spectrum based on the detected optical signal, and estimate the blood concentration of the analyte by analyzing the reconstructed sweat spectrum.

6. The apparatus of claim 5, wherein the processor is configured to estimate concentration of the analyte in the collected sweat based on the reconstructed sweat spectrum and using a sweat analyte concentration estimation model, and estimate the blood concentration of the analyte based on the estimated concentration of the analyte in the sweat using a sweat analyte concentration-blood concentration relationship model.

7. The apparatus of claim 5, wherein the processor is configured to estimate the blood concentration of the analyte based on the reconstructed sweat spectrum and using a blood concentration estimation model.

8. The apparatus of claim 1, further comprising an output interface configured to output the estimated blood concentration.

9. A method of estimating a blood concentration of an analyte, comprising:
    collecting sweat from a skin surface of a user;
    emitting light rays of different wavelengths towards the collected sweat, and detecting an optical signal reflected by the collected sweat; and
    estimating the blood concentration of the analyte based on the detected optical signal,
    wherein the estimating the blood concentration of the analyte comprises reconstructing a sweat spectrum based on the detected optical signal, and estimating the blood concentration of the analyte by analyzing the reconstructed sweat spectrum,
    wherein the estimating of the blood concentration of the analyte comprises estimating concentration of the analyte in the collected sweat based on the sweat spectrum and using a sweat analyte concentration estimation model, and estimating the blood concentration based on the estimated concentration of the analyte in the collected sweat using a sweat analyte concentration-blood concentration relationship model.

10. The method of claim 9, wherein the analyte includes at least one of glucose, triglyceride, cholesterol, protein, lactate, ethanol, uric acid, and ascorbic acid.

11. The method of claim 9, wherein the estimating of the blood concentration of the analyte comprises estimating the blood concentration of the analyte from the sweat spectrum using a blood concentration estimation model.

12. The method of claim 9, further comprising outputting the estimated blood concentration.

13. A non-transitory computer-readable medium storing instructions, the instructions comprising one or more instructions that, when executed by one or more processors of a device for estimating a blood concentration of an analyte, cause the one or more processors to:

control a sweat collector of the device to collect sweat from a skin surface of a user;

control an optical sensor of the device to emit light rays of different wavelengths towards the collected sweat, and control the optical sensor of the device to detect an optical signal reflected by the collected sweat; and estimate the blood concentration of the analyte based on the detected optical signal, wherein the one or more instructions further cause the one or more processors to:

reconstruct a sweat spectrum based on the detected optical signal;

estimate concentration of the analyte in the collected sweat based on the sweat spectrum and using as sweat analyte concentration estimation model; and estimate the blood concentration based on the estimated concentration of the analyte in the collected sweat using a sweat analyte concentration-blood concentration relationship model.

14. The non-transitory computer-readable medium of claim 13, wherein the analyte includes at least one of glucose, triglyceride, cholesterol, protein, lactate, ethanol, uric acid, and ascorbic acid.

15. The non-transitory computer-readable medium of claim 13, wherein the one or more instructions further cause the one or more processors to:

control a display of the device to display the estimated blood concentration.

* * * * *